United States Patent
Osawa

(10) Patent No.: US 11,529,115 B2
(45) Date of Patent: Dec. 20, 2022

(54) ULTRASOUND PROBE FOR PUNCTURE NEEDLE AND ULTRASOUND DIAGNOSTIC DEVICE USING SAME

(71) Applicant: FUJIFILM Corporation, Tokyo (JP)

(72) Inventor: Atsushi Osawa, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1036 days.

(21) Appl. No.: 14/867,632

(22) Filed: Sep. 28, 2015

(65) Prior Publication Data

US 2016/0015361 A1  Jan. 21, 2016

Related U.S. Application Data

(63) Continuation of application No. PCT/JP2014/050941, filed on Jan. 20, 2014.

(30) Foreign Application Priority Data

Mar. 29, 2013  (JP) .............................. JP2013-075174

(51) Int. Cl.
*A61B 8/08* (2006.01)
*A61B 8/00* (2006.01)

(52) U.S. Cl.
CPC .......... *A61B 8/0841* (2013.01); *A61B 8/4444* (2013.01); *A61B 8/461* (2013.01)

(58) Field of Classification Search
CPC .... A61M 5/427; A61B 8/0841; A61B 8/4444; A61B 8/461; A61B 8/0833; G01F 1/662
See application file for complete search history.

(56) References Cited

U.S. PATENT DOCUMENTS

| | | | | |
|---|---|---|---|---|
| 2,913,602 A | * | 11/1959 | Joy | G10K 11/32 |
| | | | | 73/644 |
| 3,661,146 A | * | 5/1972 | Peronneau | A61B 5/6876 |
| | | | | 600/453 |
| 4,127,842 A | * | 11/1978 | Hassler | A61B 8/06 |
| | | | | 367/90 |

(Continued)

FOREIGN PATENT DOCUMENTS

| | | |
|---|---|---|
| CN | 103124521 A | 5/2013 |
| GB | 1285715 A | 8/1972 |

(Continued)

OTHER PUBLICATIONS

Translation of JP 200803929 (Year: 2008).*

(Continued)

*Primary Examiner* — Amelie R Davis
*Assistant Examiner* — Helene Bor
(74) *Attorney, Agent, or Firm* — Birch, Stewart, Kolasch & Birch, LLP

(57) ABSTRACT

An ultrasound probe for a puncture needle and an ultrasound diagnostic device using the same are disclosed. The ultrasound probe for the puncture needle transmits ultrasonic waves to a subject from a transducer array which is arranged so as to be tilted at a predetermined array angle of inclination with respect to a subject contact surface, in a direction in which an angle of an ultrasonic wave transmission/reception surface with respect to a puncturing direction of the puncture needle punctured from a puncture position toward the front of the subject contact surface decreases, receives ultrasonic echoes, forms sound ray signals which are tilted to a side of the puncture needle, and generates a B mode image of a deep region of the subject from the sound ray signals.

8 Claims, 5 Drawing Sheets

(56) References Cited

U.S. PATENT DOCUMENTS

| | | | | |
|---|---|---|---|---|
| 4,413,629 | A * | 11/1983 | Durley, III | A61B 5/0011 |
| | | | | 600/453 |
| 4,430,593 | A * | 2/1984 | Gohlert | G10K 11/02 |
| | | | | 310/327 |
| 4,501,278 | A * | 2/1985 | Yamaguchi | A61B 8/0833 |
| | | | | 600/461 |
| 4,823,800 | A * | 4/1989 | Compos | A61B 8/12 |
| | | | | 73/644 |
| 5,024,094 | A * | 6/1991 | Kubota | G01S 7/52049 |
| | | | | 73/620 |
| 5,050,436 | A * | 9/1991 | Kunii | B06B 1/067 |
| | | | | 73/644 |
| 5,094,108 | A * | 3/1992 | Kim | G01N 29/041 |
| | | | | 310/335 |
| 5,360,007 | A * | 11/1994 | Shinomura | G01S 15/8952 |
| | | | | 600/447 |
| 5,992,235 | A * | 11/1999 | Fischer | G10K 11/004 |
| | | | | 73/624 |
| 8,979,776 | B2 * | 3/2015 | Gelbart | A61B 17/225 |
| | | | | 600/437 |
| 2007/0056373 | A1 * | 3/2007 | Fischer | G01N 29/07 |
| | | | | 73/609 |
| 2011/0087106 | A1 * | 4/2011 | Ridley | A61B 8/0833 |
| | | | | 600/461 |
| 2012/0270177 | A1 * | 10/2012 | Nakashima | A61C 17/20 |
| | | | | 433/215 |
| 2013/0074602 | A1 * | 3/2013 | Jackson | G01N 29/24 |
| | | | | 73/633 |
| 2013/0267849 | A1 | 10/2013 | Katsuyama | |
| 2015/0009782 | A1 * | 1/2015 | Engl | G01N 29/221 |
| | | | | 367/189 |

FOREIGN PATENT DOCUMENTS

| | | |
|---|---|---|
| JP | 55-110538 A | 8/1980 |
| JP | 57-131432 A | 8/1982 |
| JP | 11-216137 A | 8/1999 |
| JP | 2005-144028 A | 6/2005 |
| JP | 2006-288580 A | 10/2006 |
| JP | 2008-39629 A | 2/2008 |
| JP | 2008039629 A * | 2/2008 |
| JP | 2008089317 A * | 4/2008 |
| JP | 2013-507177 A | 3/2013 |

OTHER PUBLICATIONS

Pradeep Kumar Garu. Acoustic & Mechanical Properties of Neoprene Rubber for Encapsulation of Underwater Transducers. International Journal of Scientific Engineering and Technology (ISSN : 2277-1581) vol. No. 1, Issue No. 5, p. 231-237. (Year: 2012).*

And Signal Processing SA. US Data Tables. Retrieved Apr. 9, 2020, from https://www.signal-processing.com/table.php (Year: 2020).*

Corsaro, R. D. et al. "A Filled Silicone Rubber Materials System with Selectable Acoustic Properties for Molding and Coating Applications at Ultrasonic Frequencies." (1979): Web. https://doi.org/10.21236/ADA070461 (Year: 1979).*

Diederichs, R., 1997. Plastic Material's acoustic properties. [online] NDT.net. Available at: <https://www.ndt.net/links/proper.htm> [Accessed Apr. 9, 2022] (Year: 1997).*

International Preliminary Report on Patentability and English translation of the Written Opinion of the International Searching Authority (Forms PCT/IB/338, PCT/IB/373 and PCT/ISA/237), dated Oct. 8, 2015, for International Application No. PCT/JP2014/050941.

Chinese Office Action, dated Mar. 27, 2017, for Chinese Application No. 201480019486.1, including English translation.

Chinese Office Action, dated Nov. 2, 2016, for Chinese Application No. 201480019486.1, including an English translation.

International Search Report, issued in PCT/JP2014/050941, dated Mar. 11, 2014.

Extended European Search Report, dated Apr. 1, 2016, for European Patent Application No. 14776531.7.

* cited by examiner

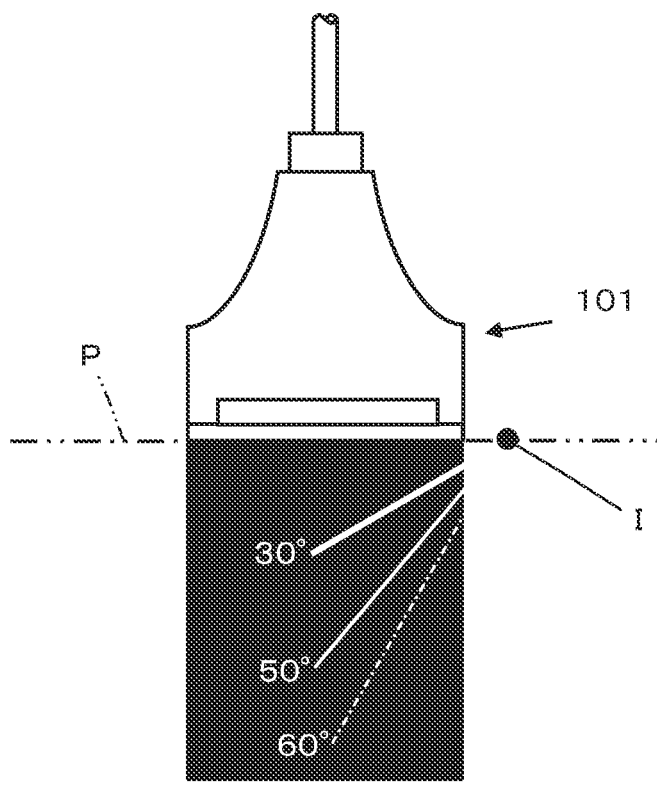

ULTRASOUND PROBE FOR PUNCTURE NEEDLE AND ULTRASOUND DIAGNOSTIC DEVICE USING SAME

CROSS-REFERENCE TO RELATED APPLICATIONS

This application is a Continuation of PCT International Application No. PCT/JP2014/050941 filed on Jan. 20, 2014, which claims priority under 35 U.S.C. § 119(a) to Japanese Patent Application No. 2013-075174 filed on Mar. 29, 2013. The above application is hereby expressly incorporated by reference, in its entirety, into the present application.

BACKGROUND OF THE INVENTION

The invention relates to an ultrasound probe and an ultrasound diagnostic device using the same, and particularly relates to an ultrasound probe for a puncture needle that is used with a puncture needle and an ultrasound diagnostic device using the same.

Conventionally, ultrasound diagnostic devices using ultrasound images are put to practical use in the medical field. Generally, this type of ultrasound diagnostic device includes an ultrasound probe having a built-in transducer array and a diagnostic apparatus main body connected to the ultrasound probe. Ultrasonic waves are transmitted from the ultrasound probe toward an inspection object (subject), ultrasonic echoes from the subject are received by the ultrasound probe, and an ultrasound image is generated by electrically processing the received signals in the diagnostic apparatus main body.

Additionally, according to the ultrasound diagnostic device, the arrangement of a puncture needle in the ultrasound probe and usage of the ultrasound diagnostic device with the puncture needle so that processing can be performed while checking the ultrasound image have been known to be useful. JP 2006-288580 A discloses a probe for a puncture needle capable of accurately checking a position of a puncture needle within a close distance.

SUMMARY OF THE INVENTION

FIG. 8 illustrates an example (hereinafter "conventional ultrasound probe 101") of an ultrasound probe frequently used with puncturing. The conventional ultrasound probe 101 is an example of a linear ultrasound probe having a 7.5-MHz center frequency and a 0.3-mm element array pitch. According to the conventional ultrasound probe 101, while it is possible to clearly draw an ultrasound image and check the position of the puncture needle on the ultrasound image with certainty when the puncture angle of the puncture needle is 30°, for example, in a shallow region (at a close distance), if an attempt is made to check the position of the puncture needle in a deep region (at a far distance) with the puncture angle of the puncture needle tilted at 50° or 60°, the ultrasound image attenuates approximately ⅓ of the value when the insertion angle is 30° at an insertion angle of 50°, and to approximately 1/30 of the value when the insertion angle is 30° at an insertion angle of 60°, making it no longer possible to clearly draw the image of the puncture needle or accurately check the position of the puncture needle.

Therefore, an object of the invention is to provide an ultrasound probe for a puncture needle and an ultrasound diagnostic device capable of clearly drawing a puncture needle in a deep region of a subject.

In order to solve the above problem, the present invention provides an ultrasound probe for a puncture needle, comprising: a transducer array having an ultrasonic wave transmission/reception surface that extends along an array direction of a plurality of transducers; a subject contact surface that is positioned in front of the ultrasonic wave transmission/reception surface of the transducer array, and contacts a subject during ultrasound diagnosis; an acoustic lens arranged on a side of the ultrasonic wave transmission/reception surface of the transducer array, wherein a puncture position of a puncture needle is set near one end of the subject contact surface, the transducer array is arranged so as to be tilted at a predetermined array angle θ of inclination with respect to the subject contact surface, in a direction in which the angle of the ultrasonic wave transmission/reception surface with respect to a puncturing direction of the puncture needle punctured from the puncture position toward the front of the subject contact surface decreases, and an outer surface of the acoustic lens is the subject contact surface.

Preferably, given a wavelength λ of ultrasonic waves in the subject, an element array pitch a of the transducer array, and a following approximation formula D(θ) of transducer directivity:

$D(\theta) = \{(\sin x)/x\} \cdot \cos \theta$ $x = (\pi a/\lambda) \cdot \sin \theta$ an array angle θ of inclination satisfies:

$D(\theta)/D(0°) < 1/10$ and $a < \lambda/(1 + |\sin \theta|)$.

Further, given a wavelength λ of ultrasonic waves in the subject, an element array pitch a of the transducer array, and a following approximation formula D(θ) of transducer directivity:

$D(\theta) = \{(\sin x)/x\} \cdot \cos \theta$ $x = (\pi a/\lambda) \cdot \sin \theta$ an array angle θ of inclination may satisfy:

$D(\theta)/D(0°) \approx 1/10$ and $a < \lambda/(1 + |\sin \theta|)$.

Preferably, a wedge-shaped filling member having a sound attenuation rate less than that of an acoustic lens is arranged between the transducer array and the acoustic lens.

Preferably, a sound velocity of the wedge-shaped filling member is slower than a sound velocity of the acoustic lens.

Preferably, the transducer array further comprises a sound matching layer arranged on the wedge-shaped filling member side; and the wedge-shaped filling member has a smaller acoustic impedance than that of the sound matching layer.

In addition, the present invention provides an ultrasound diagnostic device, comprising: the ultrasound probe for a puncture needle described above; and a diagnostic apparatus main body connected to the ultrasound probe for the puncture needle, wherein: the diagnostic apparatus main body includes: a transmission driving section that supplies a driving signal to the transducer array of the ultrasound probe to transmit ultrasonic beams toward a subject; a transmission controller that forms ultrasonic beams by imparting a predetermined transmission delay amount to the driving signal supplied to the transmission driving section; a reception signal processor that generates reception data from a reception signal output from the transducer array of the ultrasound probe that received ultrasonic echoes from a subject; a phasing addition section that generates a sound ray signal by imparting a predetermined reception delay amount on the reception data and performing addition processing; a signal processor that performs attenuation correction in accordance with a focal position of ultrasonic waves on the sound ray signal; and a correction table storage having a correction table that describes the transmission delay amount, the reception delay amount, and the attenuation correction amount based on the focal position, individually calculated in advance in accordance with an arrangement of the transducers and the focal position, and wherein the transmission controller imparts the predetermined transmission delay amount on the driving signal on the basis of the correction table stored in the correction table storage, and forms the ultrasonic beams, the phasing addition section generates the sound ray signal by imparting the predetermined reception delay amount on the reception data on the basis of the correction table stored in the correction table storage, and performing addition processing, and the signal processor performs the attenuation correction on the basis of the correction table stored in the correction table storage.

Further, the present invention provides an ultrasound diagnostic device comprising: the ultrasound probe for a puncture needle described above; and a diagnostic apparatus main body connected to the ultrasound probe for the puncture needle, wherein a diagnostic apparatus main body connected to the ultrasound probe for a puncture needle, wherein the diagnostic apparatus main body includes: a transmission driving section that supplies a driving signal to the transducer array of the ultrasound probe to transmit ultrasonic beams toward a subject; a transmission controller that forms ultrasonic beams by imparting a predetermined transmission delay amount to the driving signal supplied to the transmission driving section; a reception signal processor that generates reception data from a reception signal output from the transducer array of the ultrasound probe that received ultrasonic echoes from the subject; a phasing addition section that generates a sound ray signal by imparting a predetermined reception delay amount on the reception data and performing addition processing; a signal processor that performs attenuation correction in accordance with a focal position of ultrasonic waves on the sound ray signal, and a high-speed calculation processor that individually calculates the transmission delay amount, the reception delay amount; and an attenuation correction amount based on the focal position, in accordance with an arrangement of the transducers and the focal position.

Preferably, the high-speed calculation processor serves as the phasing addition section and the signal processor.

According to the invention, it is possible to clearly draw a puncture needle, even in a deep region of a subject, on an ultrasound image, and accurately identify the position of the puncture needle in the deep region of the subject. As a result, it is possible to prevent erroneous puncture, improve the puncture limiting angle, and perform puncturing with diseases located in a deep region of the subject.

BRIEF DESCRIPTION OF THE DRAWINGS

FIG. 8 is an explanatory view of an ultrasound image that includes a puncture needle drawn when a conventional ultrasound probe for a puncture needle is used.

DETAILED DESCRIPTION OF THE INVENTION

The following is a detailed description of the ultrasound probe and ultrasound diagnostic device according to the invention based on the preferred embodiments illustrated in the accompanying drawings.

Embodiment 1

Figure 1:
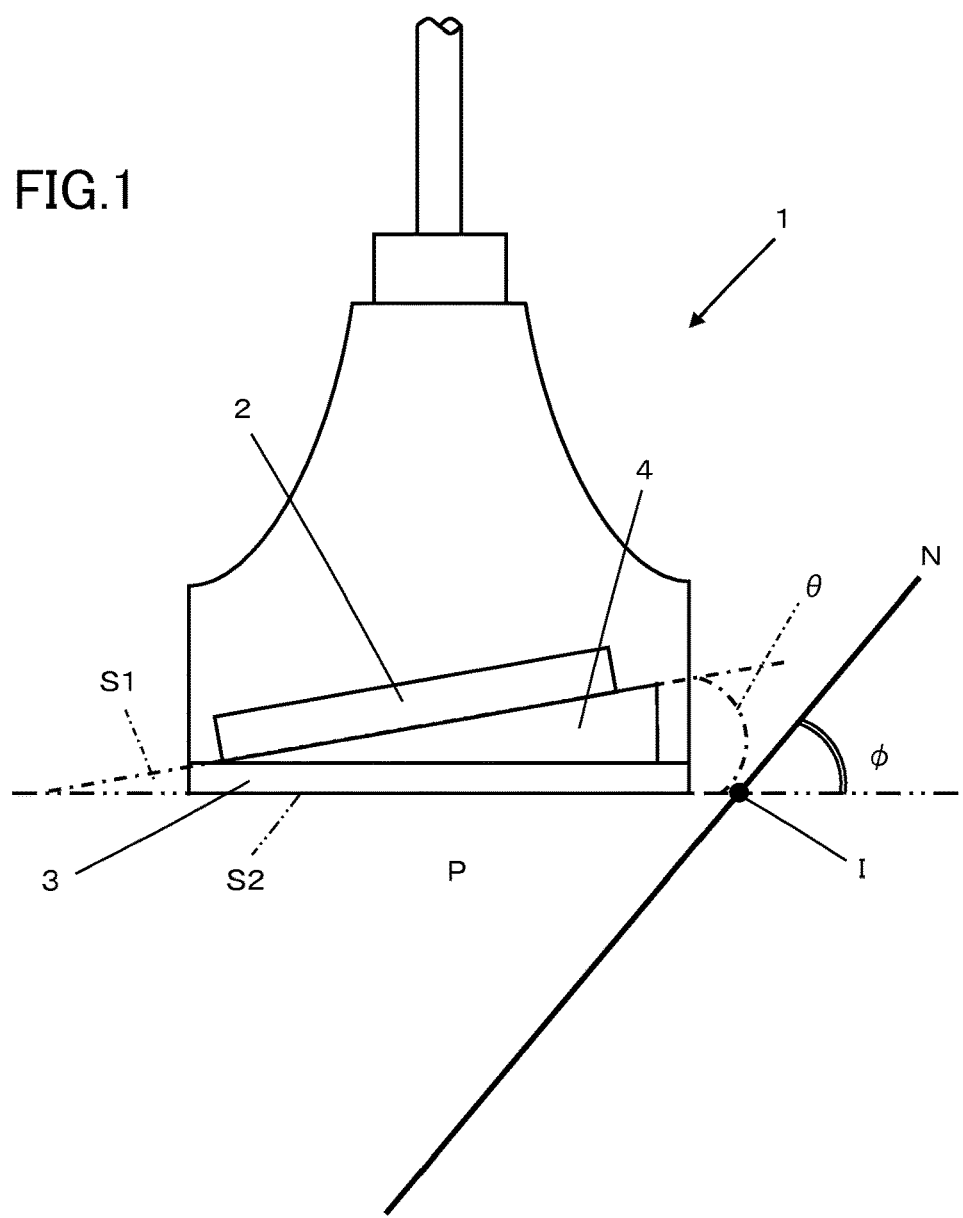
FIG. 1 is a schematic view illustrating the configuration of an ultrasound probe for a puncture needle according to an embodiment 1 of the invention.

FIG. 1 is a schematic view illustrating the configuration of the ultrasound probe for a puncture needle according to the embodiment 1 of the invention.

An ultrasound probe 1 for a puncture needle according to the embodiment 1 includes a transducer array 2 having an ultrasonic wave transmission/reception surface S1 that extends along an array direction of a plurality of transducers, an acoustic lens 3 having a subject contact surface S2 that is arranged on the ultrasonic wave transmission/reception surface S1 side of the transducer array 2, that is, in front of the transducer array 2, and contacts a subject P during ultrasound diagnosis, and a wedge-shaped filling member 4 arranged between the transducer array 2 and the acoustic lens 3. In the ultrasound probe 1 for a puncture needle, a puncture position I of a puncture needle N is set near one end of the subject contact surface S2, and the puncture needle N is attached at a predetermined puncture angle φ by a puncture needle holder (not illustrated).

The transducer array 2 is disposed so as to be tilted at a predetermined array angle θ of inclination with respect to the subject contact surface S2 in a direction in which the angle of the ultrasonic wave transmission/reception surface S1 with respect to the puncturing direction of the puncture needle N punctured from the puncture position I toward the front of the subject contact surface S2 decreases, that is, so that the ultrasonic wave transmission/reception surface S1 faces the puncture position I.

Figure 2:
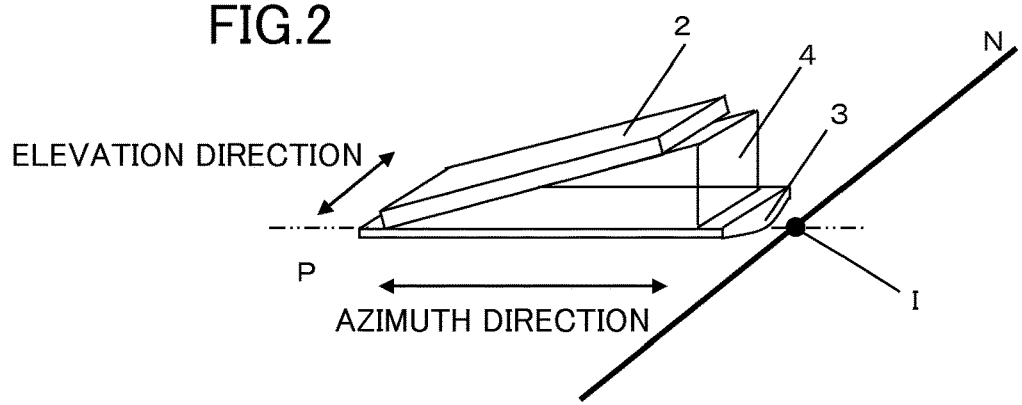
FIG. 2 is a perspective view of the ultrasound probe for a puncture needle according to the embodiment 1 of the invention.

FIG. 2 is a perspective view of the ultrasound probe 1 for a puncture needle illustrated in FIG. 1. The puncture position of the puncture needle N is positioned in a center in an elevation direction of the transducer array 2, and the puncture needle N enters from an azimuth direction of the transducer array 2, puncturing the subject P so as to pass through the center in the elevation direction of the transducer array 2.

Accordingly, when ultrasonic beams are transmitted in a direction perpendicular to the ultrasonic wave transmission/reception surface S1 by the ultrasound probe 1 according to the embodiment 1, it is possible to transmit ultrasonic beams that are more perpendicular with respect to the puncture needle N and receive clearer ultrasonic echoes from the puncture needle N compared to the ultrasonic beams from a conventional ultrasound probe in which the ultrasonic wave transmission/reception surface and subject contact surface are parallel. This point physically differs from when the transducer array is scanned and the ultrasonic beams are steered in a conventional ultrasound diagnosis.

The transducer array 2 is made of a plurality of transducers linearly arranged at an equal interval at a predetermined pitch a, and each transducer is configured to form an electrode on both ends of a piezoelectric body made from, for example, piezoelectric ceramic represented by lead zirconate titanate (PZT), polymer piezoelectric elements represented by polyvinylidene fluoride (PVDF), or the like.

When a voltage in pulse form or in the form of a continuous wave is applied to the electrodes of this type of transducer, the piezoelectric body is constricted, an ultrasonic wave in pulse form or continuous wave form is generated from each transducer, and an ultrasonic beam is formed by the synthesis of these ultrasonic waves. In addition, each transducer receives a propagating ultrasonic wave and as a result expands and contracts, thereby generating an electrical signal. These electrical signals are output as ultrasound reception signals.

The acoustic lens 3 is arranged in front of the transducer array 2 and, during ultrasound diagnosis, an outer surface S2 thereof directly contacts the subject P. The acoustic lens 3 is, for example, formed by silicone rubber, and is for focusing the ultrasonic beams transmitted from the transducer array 2 at a predetermined depth within the subject P.

The wedge-shaped filling member 4 is a wedge-shaped member for tilting the ultrasonic wave transmission/reception surface S1 of the transducer array 2 at an array angle θ of inclination with respect to the outer surface S2 of the acoustic lens 3, and propagates the ultrasonic waves generated by the transducer array 2 as well as the ultrasonic echoes from within the subject P. The wedge-shaped filling member 4 is, for example, formed by silicone rubber, urethane synthetic resin, epoxy, or the like.

Next, the operation of the ultrasound probe 1 for a puncture needle according to the embodiment 1 will be described.

Figure 3:
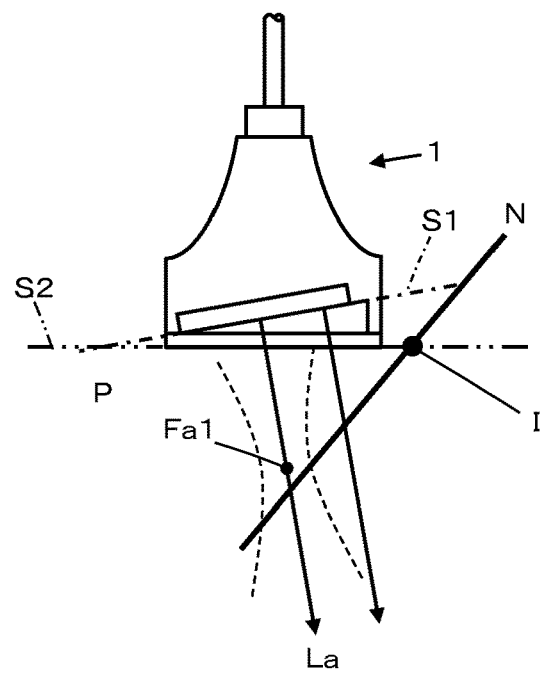
FIG. 3 is an explanatory view schematically explaining the relationship between sound ray signals formed when the ultrasound probe for a puncture needle according to the invention transmits ultrasonic beams and receives ultrasonic echoes, and the focal position.

As illustrated in FIG. 3, ultrasonic waves are transmitted from the transducer array 2 arranged so as to be tilted at a predetermined array angle θ of inclination with respect to the subject P, ultrasonic beams are formed with respect to a focal position Fa1, for example, ultrasonic echoes are received in the transducer array 2, and sound ray signals La are formed.

Figure 4:
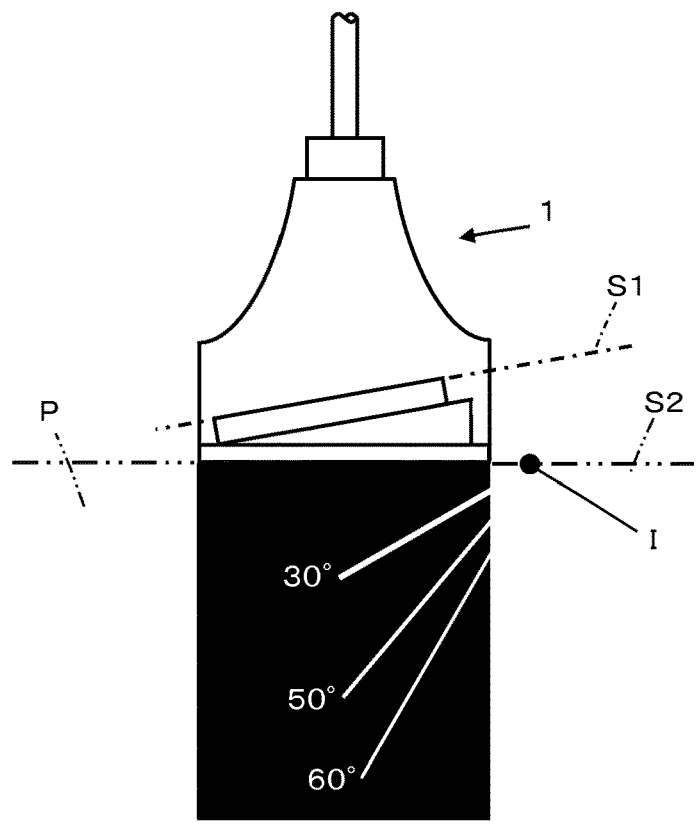
FIG. 4 is an explanatory view of an ultrasound image that includes a puncture needle drawn when the ultrasound probe for a puncture needle according to the embodiment 1 of the invention is used.

The sound ray signals La are formed so as to be tilted to the puncture needle N side compared to the sound ray signals formed by a conventional ultrasound probe. Thus, even if, for example, the puncture needle N reaches a deep region of the subject P at an incline of 50°, 60°, or the like, the ultrasonic echoes from the puncture needle N can be more clearly received in the transducer array 2 and, as illustrated in FIG. 4, a B mode image of the deep region of the subject P that includes the puncture needle N can be more clearly drawn compared to a conventional ultrasound probe.

Given a wavelength λ of the ultrasonic waves in a human body (subject P), an approximation formula D(θ) of transducer directivity, which indicates the relative sound pressure value toward a direction of the angle θ of the transducer, is expressed as the following formula (1).

$$D(\theta)=\{(\sin x)/x\}\cdot \cos \theta, x=(\pi a/\lambda)\cdot \sin \theta \quad (1)$$

As general evaluation criteria, a satisfactory image for ultrasound diagnosis can be created if the amount of sensitivity reduction of ultrasonic echoes is −20 dB or less.

Now, given that the ultrasound probe 1 for a puncture needle according to the invention is a linear ultrasound probe having a 7.5-MHz center frequency and a 0.3-mm element array pitch a, which is similar to the conventional ultrasound probe 101, if the incline of the puncture needle N is 60°, D(θ=30°)/D(0°) is 1/10 (−20 dB), D(θ=50°)/D(0°) is 1/30 (−30 dB), and D(θ=60°)/D(0°) is 1/300 (−50 dB) compared to when the incline of the puncture needle N is 30° as illustrated in the conventional ultrasound image in FIG. 8, and therefore the ultrasound image (B mode image) attenuates to approximately 1/30.

Accordingly, in the embodiment 1 of the invention, when the amount of sensitivity reduction of an image range to be observed is increased by at least −20 dB, that is, by setting the array angle θ of inclination to 10° and tilting the ultrasonic wave transmission/reception surface S1 of the transducer array 2 at 10° to the puncture needle N side with respect to the outer surface S2 of the acoustic lens, it is possible to improve the amount of sensitivity reduction at D(θ=60°) by −20 dB and make the B mode image when the incline of the puncture needle N of the invention is 60° the same as the B mode image when the incline of a conventional puncture needle N is 50°.

Additionally, the array angle θ of inclination has an upper limit. The upper limit of the array angle θ of inclination is expressed by the following formula (2).

$$a<\lambda/(1+|\sin \theta|) \quad (2)$$

Formula (2) is determined by a grating lobe that occurs in the ultrasound probe 1.

The reason is that, during imaging, a steering process is performed to execute conventional imaging, but when the range of θ expressed in this formula (2) is exceeded in the steering process and the transducer array is tilted, the grating lobe actually becomes too large, leading to the generation of a virtual image on the image.

As a result, given that the ultrasound probe 1 for a puncture needle according to the invention is a linear ultrasound probe having a 7.5-MHz center frequency and a 0.3-mm transducer element array pitch, the array angle θ of inclination of the transducer array 2 for more clearly drawing a deep region of the subject P is preferably about 8° to 15°, and most preferably about 10°, based on the aforementioned formulas (1) and (2).

As a result, according to the ultrasound probe 1 for a puncture needle according to the embodiment 1, it is possible to improve the puncture visibility as well as the puncture limiting angle (the limiting angle at which the puncture needle can be visually confirmed), thereby preventing erroneous puncture and making it possible to perform puncturing with diseases located in a deep region of the subject.

Embodiment 2

Figure 5:
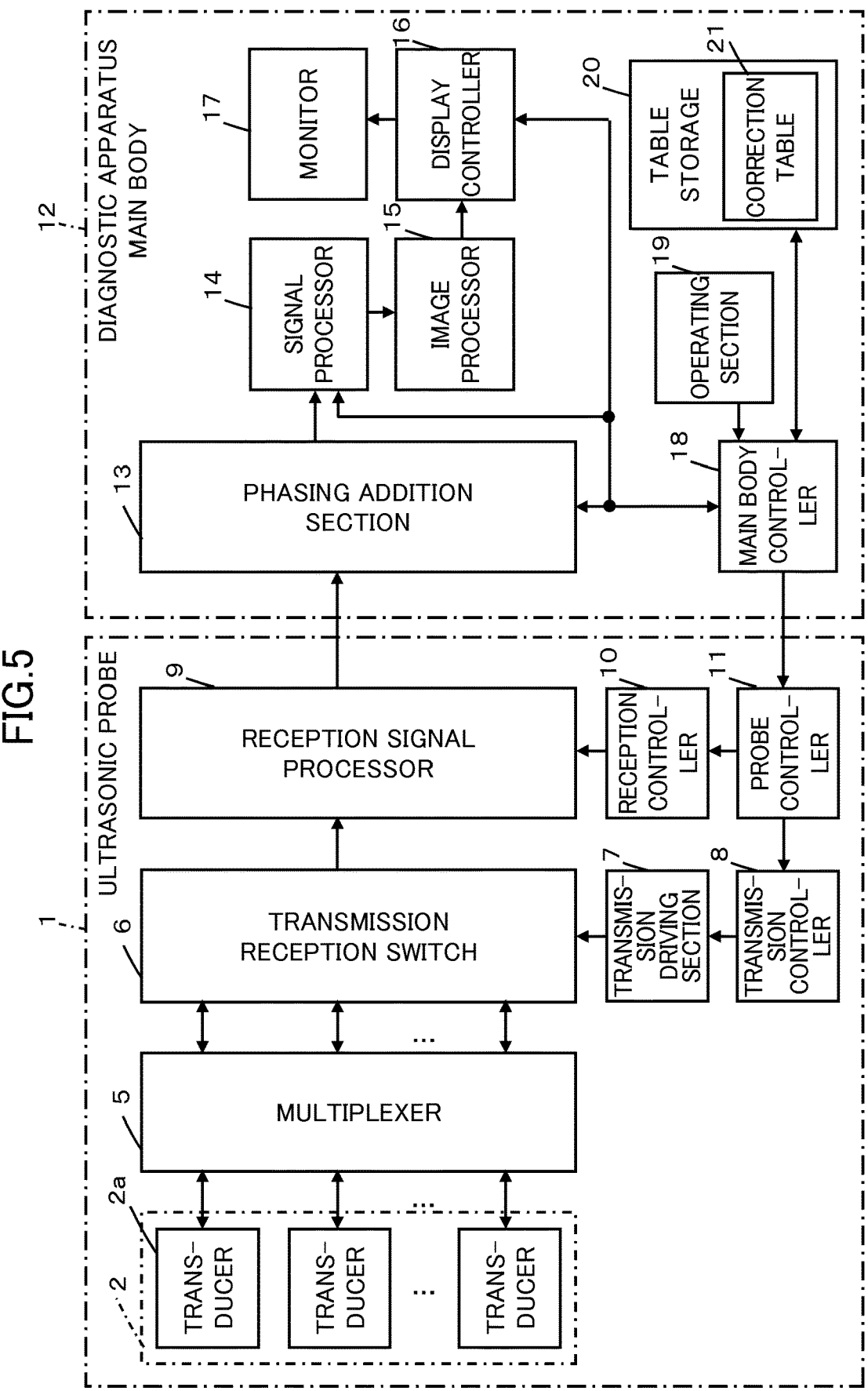
FIG. 5 is a block diagram illustrating the overall configuration of the ultrasound diagnostic device according to an embodiment 2 of the invention.

FIG. 5 is a block diagram illustrating the overall configuration of the ultrasound diagnostic device according to the embodiment 2 of the invention that includes the aforementioned ultrasound probe 1 for a puncture needle.

The ultrasound diagnostic device according to the embodiment 2 is made of the ultrasound probe 1 for a puncture needle (hereinafter, "ultrasound probe 1") and a diagnostic apparatus main body 12 connected to each other, wherein the ultrasound probe 1 includes the transducer array 2 made of a plurality of transducers 2a linearly arranged at an equal interval, a multiplexer 5 interconnected with each of the transducers 2a of the transducer array 2, a transmission/reception switch 6 interconnected with the multiplexer 5, a transmission driving section 7 and transmission controller 8 which are connected sequentially from the transmission/reception switch 6, a reception signal processor 9 connected to the transmission/reception switch 6, a reception controller 10 connected to the reception signal processor 9, and a probe controller 11 connected to the reception controller 10 as well as the transmission controller 8.

Additionally, the diagnostic apparatus main body 12 includes a phasing addition section 13; a signal processor 14, an image processor 15, a display controller 16, and a monitor 17 connected sequentially from the phasing addition section 13; a main body controller 18 interconnected with the phasing addition section 13, the signal processor 14, and the display controller 16; an operating section 19 connected to the main body controller 18; and a table storage 20 interconnected with the main body controller 18. The table storage 20 includes a correction table 21 in the interior, the phasing addition section 13 is connected from the reception signal processor 9 of the ultrasound probe 1, and the main body controller 18 is interconnected with the probe controller 11 of the ultrasound probe 1.

The plurality of transducers 2a that constitutes the transducer array 2 transmits ultrasonic waves on the basis of driving signals supplied from the transmission driving section 7 via the transmission/reception switch 6 and the multiplexer 5, receives ultrasonic echoes from the subject, and outputs reception signals.

The multiplexer 5 switches the plurality of transducers 2a that transmits ultrasonic waves on the basis of an instruction from the probe controller 11 via the transmission controller 8 or the reception controller 10, and switches the plurality of transducers 2a that receives ultrasonic echoes.

The transmission/reception switch 6 switches the connections between the multiplexer 5, the transmission driving section 7, and the reception signal processor 9 so as to connect the transmission driving section 7 and the multiplexer 5 and disconnect the reception signal processor 9 and the multiplexer 5 when the driving signal supplied from the transmission driving section 7 is transmitted to the transducer array 2, and connect the reception signal processor 9 and the multiplexer 5 and disconnect the transmission driving section 7 and the multiplexer 5 when the reception signal processor 9 acquires a reception signal from the transducer array 2, on the basis of an instruction from the probe controller 11 via the transmission controller 8 or the reception controller 10.

The transmission driving section 7 includes, for example, a plurality of pulse generators and, on the basis of the transmission delay pattern selected by the transmission controller 8, adjusts the amount of delay of each driving signal so as to form wide ultrasonic beams in which the ultrasonic waves transmitted from the plurality of transducers 2a cover an area of tissue within the subject, and supplies the driving signals to the plurality of transducers 2a. Here, the transmission delay pattern is a pattern of the transmission delay amount set in each of the transducers 2a, in the transmission of the ultrasonic waves based on the driving signal.

The transmission controller 8 selects one of a plurality of transmission delay patterns stored in an internal memory (not illustrated) of the transmission driving section 7 on the basis of an instruction from the probe controller 11, and imparts a predetermined delay amount on the driving signal imparted on each of the transducers 2a from the transmission driving section on the basis of the transmission delay pattern. Additionally, the plurality of transmission delay patterns stored in the internal memory (not illustrated) of the transmission driving section 7 is stored within the internal memory (not illustrated) of the transmission driving section 7 by the transmission controller 8. Further, the transmission controller 8 controls the switching to the transmission driving section 7 side of the transmission/reception switch 6 on the basis of an instruction from the probe controller 11 as well.

The reception signal processor 9 includes a low-noise amplifier (LNA), an arc tangent (ATN) circuit, and an analog-to-digital (A/D) converter. The reception signal processor 9, under the instruction of the reception controller 10, generates complex base band signals by processing the reception signal output from the corresponding transducer 2a, converting the signal to a digital reception signal, and performing quadrature detection processing or quadrature sampling processing on the digital reception signal, and generates sample data that includes information on an area of tissue by sampling the complex base band signals. The generated sample data is output to the phasing addition section 13 of the diagnostic apparatus main body 12.

The reception controller 10 controls the reception signal processor 9, converts the reception signal output from the transducer 2a to sample data, and outputs the result to the phasing addition section 13 of the diagnostic apparatus main body 12, on the basis of an instruction from the probe controller 11. Further, the reception controller 10 controls the switching to the reception signal processor 9 side of the transmission/reception switch 6 on the basis of an instruction from the probe controller 11 as well.

The probe controller 11 controls each component of the ultrasound probe 1 on the basis of the various control signals transmitted from the main body controller 18 of the diagnostic apparatus main body 12. As described above, the probe controller 11 controls the transmission controller 8 and the reception controller 10 as described above so that ultrasonic waves are transmitted from the transducer array 2, and ultrasonic echoes are received in the transducer array 2.

The phasing addition section 13 of the diagnostic apparatus main body 12 acquires the sample data that includes information on the area of tissue from the reception signal processor 9 of the ultrasound probe 1 and, in accordance with the reception direction (here, the direction perpendicular to the ultrasonic wave transmission/reception surface) set in the probe controller 11 of the ultrasound probe 1, selects one reception delay pattern from the plurality of reception delay patterns stored in the internal memory (not illustrated) of the phasing addition section 13, and imparts and adds each reception delay amount to the plurality of complex base band signals indicated by the reception data based on the selected reception delay pattern, thereby forming a beam in response to the plurality of reception data having a time difference generated by the reception signal processor 9, in accordance with each of the transducers 2a. A base band signal (sound ray signal) in which the focal points of ultrasonic echoes have been narrowed down is generated through this beam formation. Here, the reception delay pattern is a pattern of a reception delay amount individually imparted on the reception data acquired by each transducer 2a for generating sound ray signals.

The signal processor 14 generates a B-mode image signal, which is tomographic image information related to the tissue within the subject P, by correcting the attenuation resulting from the distance in accordance with the depth of the reflection position of the ultrasonic waves, and subsequently converting the sound ray signals generated by the phasing addition section 13 to image signals (raster conversion) in accordance with a regular scanning method of a television signal. The generated B-mode image signal is output to the image processor 15.

The image processor 15 performs predetermined image processing on the B-mode image signal generated by the signal processor 14. The predetermined image processing is, for example, image processing required for improving the visibility of the ultrasound image, such as gradation processing or enhancement processing. The B-mode image data subjected to image processing is output to the display controller 16 and stored in an image storage (not illustrated).

The display controller 16 displays an ultrasound image on the monitor 17 on the basis of the B-mode image signal that was subjected to image processing and output by the image processor 15.

The monitor 17 is, for example, a display apparatus such as a liquid crystal display (LCD), and displays ultrasound images under the control of the display controller 16.

The main body controller 18 controls each component of the diagnostic apparatus main body 12 on the basis of an operator's instruction from the operating section 19, acquires a plurality of transmission delay patterns, a plurality of reception delay patterns, and an attenuation correction amount in accordance with depth from the correction table 21 of the table storage 20, and outputs the acquired information to the transmission driving section 7, the phasing addition section 13, and the internal memory (not illustrated) of the signal processor 14, respectively.

The operating section 19 is configured to issue various instructions by an operator to an ultrasound diagnostic device made of the ultrasound probe 1 and the diagnostic apparatus main body 12.

The table storage 20 is configured to store the correction table 21 in which a pre-calculated plurality of transmission delay patterns, plurality of reception delay patterns, and attenuation correction amounts in accordance with depth are recorded, and output the various information recorded in the correction table 21 on the basis of an instruction from the main body controller 18.

With the transducer array 2 arranged so that the ultrasonic wave transmission/reception surface S1 thereof is tilted at an angle θ of inclination with respect to the outer surface S2 of the acoustic lens, the required transmission delay amount, reception delay amount, and attenuation correction amount differ for each transducer 2a per combination of sound ray signal and focal position, that is, depth within the subject P, making the pre-calculated plurality of transmission delay patterns, plurality of reception delay patterns, and attenuation correction amounts in accordance with depth recorded in the correction table 21 very high in number.

Although the phasing addition section 13, the signal processor 14, the image processor 15, the display controller 16, and the main body controller 18 in such diagnostic apparatus main body 12 are constituted by a central processing unit (CPU) and an operation program for causing the CPU to carry out various types of processes, these sections may instead be constituted by digital circuitry. These operation programs are stored in a storage unit (not illustrated) in the diagnostic apparatus main body 12. For the storage medium of the storage unit (not illustrated), a flexible disk, a magneto-optical disk (MO), a magnet tape (NT), a random access memory (RAM), a compact disk read only memory (CD-ROM), a digital versatile disk read only memory (DVD-ROM), or the like may be used in addition to a built-in hard disk.

Next, the operation of the embodiment 1 will be described.

When an ultrasound diagnosis is started, the probe controller 11 switches the transmission/reception switch 6 via the reception controller 10, connects the multiplexer 5 and the transmission driving section 7, outputs driving signals from the transmission driving section 7 to the transducer array 2 via the multiplexer 5, and transmits ultrasonic waves from the plurality of transducers 2a constituting the transducer array 2 in accordance with these driving signals.

It should be noted that the transmission driving section 7 includes an internal memory (not illustrated) and stores the plurality of transmission delay patterns corresponding to the angle θ of inclination of the ultrasonic wave transmission/reception surface of the transducer array 2 described in the correction table 21 of the table storage 20 via the main body controller 18, and a predetermined transmission delay amount is set per transducer 2a on the basis of the transmission delay pattern selected by the transmission driving section 7 for the driving signals transmitted from the transmission driving section 7 to the transducer array 2.

When the transmission of ultrasonic waves from the plurality of transducers 2a ends, the probe controller 11 switches the transmission/reception switch 6 to the reception signal processor 9 side, connects the multiplexer 5 and the reception signal processor 9, and outputs reception signals from the transducer 2a connected by the multiplexer 5 to the reception signal processor 9.

The reception signal processor 9 processes the reception signals, converts the signals to digital reception signals, generates complex base band signals by quadrature detection processing or quadrature sampling processing, and samples the complex base band signals, thereby generating sample data that includes information on an area of tissue. The generated sample data is output to the phasing addition section 13 of the diagnostic apparatus main body 12.

The phasing addition section 13 selects one reception delay pattern from the plurality of reception delay patterns stored in the internal memory (not illustrated) of the phasing addition section 13 in accordance with the reception direction (here, the direction perpendicular to the ultrasonic wave transmission/reception surface) set in the probe controller 11 of the ultrasound probe 1, and imparts and adds each reception delay amount to the plurality of complex base band signals indicated by the reception data on the basis of the selected reception delay pattern, thereby forming a beam in response to the plurality of reception data having a time difference generated by the reception signal processor 9, in accordance with each of the transducers 2a. The sound ray signals generated by the phasing addition section 13 according to the beam formation are output to the signal processor 14.

It should be noted that the plurality of reception delay patterns is configured to correspond to the angle θ of inclination of the ultrasonic wave transmission/reception surface of the transducer array 2 described in the correction table 21 of the table storage 20, and is stored in the internal memory (not illustrated) of the phasing addition section 13 via the main body controller 18, in the same manner as the plurality of transmission delay patterns described above.

In the signal processor 14, attenuation correction processing that corrects attenuation in accordance with the depth of the reflection position of the ultrasonic waves is performed on the sound ray signals acquired from the phasing addition section 13. The attenuation correction amount used in the attenuation correction is an attenuation correction amount stored in the correction table 21 of the table storage 20, and is stored in advance in the internal memory (not illustrated) of the signal processor 14 via the main body controller 18. The signal processor 14 generates a B-mode image signal by performing raster conversion on the sound ray signals subjected to attenuation correction processing. The generated B-mode image signal is output to the image processor 15.

The image processor 15 performs predetermined image processing on the B-mode image signal output by the signal processor 14, and outputs the B-mode image signal subjected to image processing to the display controller 16.

The display controller 16 outputs the B-mode image signal subjected to image processing on the basis of an instruction from the main body controller 18 to the monitor 17, and the monitor 17 displays an ultrasound image, which is the B mode image based on the B-mode image signal.

It should be noted that, as a modification of the ultrasound probe 1 for a puncture needle according to the embodiment 1, the transducer array 2 may include a sound matching layer (not illustrated) on the ultrasonic wave transmission/reception surface S1. Here, the sound matching layer is a member for matching the acoustic impedance between the transducer array 2, the wedge-shaped filling member 4 that contacts the transducer array 2, the acoustic lens 3, and the subject. The sound matching layer (not illustrated) of the transducer array 2 has an acoustic impedance greater than that of the wedge-shaped filling member 4. For the sound matching layer (not illustrated), various known members capable of attaining the matching of acoustic impedance can be used.

Figure 6:
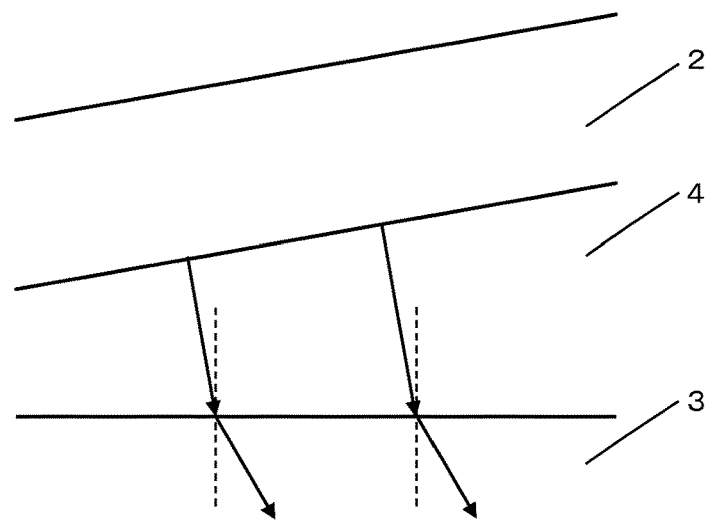
FIG. 6 is an explanatory view explaining the refraction of ultrasonic waves transmitted from transducer arrays of the ultrasound probe for a puncture needle according to a modification of the embodiment 1 of the invention, between a wedge-shaped filling member and an acoustic lens.

Additionally, the wedge-shaped filling member 4 preferably has a lower sound attenuation rate than that of the acoustic lens 3. Additionally, the sound velocity of the wedge-shaped filling member 4 is preferably slower than the sound velocity of the acoustic lens 3. When this sound velocity condition is satisfied, the ultrasonic waves transmitted from the transducer array 2 can be further tilted to the puncture needle N side as illustrated in FIG. 6, the ultrasonic echoes from the puncture needle N in the deep region of the subject P can be more clearly received, and the ultrasound image can be more clearly drawn, because of the refractive index relationship between the wedge-shaped filling member 4 and the acoustic lens 3.

Figure 7:
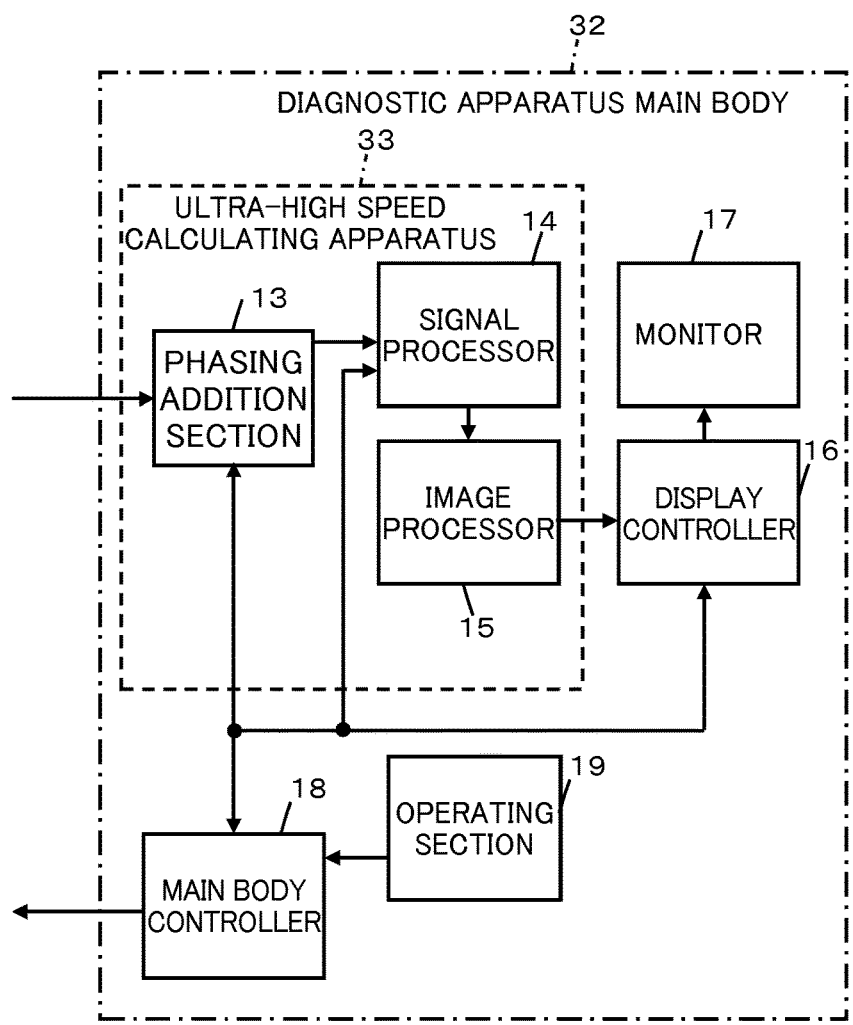
FIG. 7 is a block diagram illustrating the overall configuration of the diagnostic apparatus main body according a modification of the embodiment 2 of the invention.

Additionally, as a modification of the ultrasound diagnostic device according to the embodiment 2, the phasing addition section 13, the signal processor 14, and the image processor 15 of a diagnostic apparatus main body 32 may be configured by an ultra-high speed calculating apparatus 33 as shown in FIG. 7.

In this case, the transmission delay amount, reception delay amount, and attenuation correction amount can be calculated in real-time by the ultra-high speed calculating apparatus 33, making it possible for the main body controller 18 to proceed with each process without referring to the correction table 21 of the table storage 20. Accordingly, in the diagnostic apparatus main body 32, the table storage 20 and the correction table 21, which store large amounts of data pertaining to the transmission delay amount, reception delay amount, and attenuation correction amount, can be rendered unnecessary.

The ultrasound probe for a puncture needle and the ultrasound diagnostic device that uses the same of the invention have been described in detail hereinabove, but the invention is not limited to the aforementioned embodiments, and various improvements and changes may be made without departing from the scope of the invention.

What is claimed is:

1. A system including an ultrasound probe and a puncture needle, comprising:
   a puncture needle; and
   an ultrasound probe, the ultrasound probe including:
      a transducer array having an ultrasonic wave transmission/reception surface that extends along an array direction of a plurality of transducers;
      a subject contact surface that is positioned in front of the ultrasonic wave transmission/reception surface of the transducer array, and contacts a subject during ultrasound diagnosis;
      an acoustic lens arranged on a side of the ultrasonic wave transmission/reception surface of the transducer array and configured to focus ultrasonic beams transmitted from the transducer array at a predetermined depth within the subject;
      a wedge-shaped filling member arranged between the transducer array and the acoustic lens; and
      a probe housing that accommodates the transducer array, the acoustic lens and the wedge-shaped filling member, and extends in a direction orthogonal to the subject contact surface, wherein
   one end of the transducer array in an azimuth direction is lifted by the wedge-shaped filling member so that the transducer array is arranged in the probe housing so as to be tilted at a predetermined array angle θ of inclination with respect to the subject contact surface,
   an inner surface of the acoustic lens is a flat surface, and an outer surface of the acoustic lens is a convex curved surface that is curved only with respect to an elevation direction of the transducer array,
   a surface on the acoustic lens side of the wedge-shaped filling member is a plane parallel to the inner surface of the acoustic lens,
   the ultrasonic beams transmitted from the transducer array pass through the wedge-shaped filling member in the transmission direction of the ultrasonic beams and are focused at the predetermined depth within the subject,
   the outer surface of the acoustic lens is the subject contact surface, and
   the wedge-shaped filling member is formed by silicone rubber, urethane synthetic resin, or epoxy, and has a sound attenuation rate less than that of the acoustic lens.

2. The system including the ultrasound probe and the puncture needle according to claim 1, wherein given a wavelength λ of ultrasonic waves in the subject, an element array pitch a of the transducer array, and a following approximation formula D(θ) of transducer directivity:

$$D(\theta) = \{(\sin x)/x\} \cdot \cos \theta$$

$$x = (\pi a/\lambda) \cdot \sin \theta$$

the predetermined array angle θ of inclination satisfies:

$$D(\theta)/D(0°) < 1/10$$

and $$a < \lambda/(1+|\sin \theta|).$$

3. The system including the ultrasound probe and the puncture needle according to claim 1, wherein given a wavelength λ of ultrasonic waves in the subject, an element array pitch a of the transducer array, and a following approximation formula D(θ) of transducer directivity:

$D(\theta) = \{(\sin x)/x\} \cdot \cos \theta$ $x = (\pi a/\lambda) \cdot \sin \theta$ the predetermined array angle θ of inclination satisfies:

$D(\theta)/D(0°) \approx 1/10$ and $a < \lambda/(1+|\sin \theta|)$.

4. The system including the ultrasound probe and the puncture needle according to claim 1, wherein a sound velocity of the wedge-shaped filling member is slower than a sound velocity of the acoustic lens.

5. The system including the ultrasound probe and the puncture needle according to claim 1, wherein the transducer array further comprises a sound matching layer arranged on a side of the wedge-shaped filling member; and
the wedge-shaped filling member has a smaller acoustic impedance than that of the sound matching layer.

6. An ultrasound diagnostic device comprising:
the system including the ultrasound probe and the puncture needle according to claim 1; and
a diagnostic apparatus main body connected to the ultrasound probe for the puncture needle, wherein
the diagnostic apparatus main body includes:
  a transmission driving section that supplies a driving signal to the transducer array of the ultrasound probe to transmit ultrasonic beams toward the subject;
  a transmission controller that forms ultrasonic beams by imparting a predetermined transmission delay amount to the driving signal supplied to the transmission driving section;
  a reception signal processor that generates reception data from a reception signal output from the transducer array of the ultrasound probe that received ultrasonic echoes from the subject;
  a phasing addition section that generates a sound ray signal by imparting a predetermined reception delay amount on the reception data and performing addition processing;
  a signal processor that performs attenuation correction in accordance with a focal position of ultrasonic waves on the sound ray signal; and
  a correction table storage having a correction table that describes the transmission delay amount, the reception delay amount, and the attenuation correction amount based on the focal position, individually calculated in advance in accordance with an arrangement of the transducers and the focal position, and
wherein
the transmission controller imparts the predetermined transmission delay amount on the driving signal on the basis of the correction table stored in the correction table storage, and forms the ultrasonic beams,
the phasing addition section generates the sound ray signal by imparting the predetermined reception delay amount on the reception data on the basis of the correction table stored in the correction table storage, and performing addition processing, and
the signal processor performs the attenuation correction on the basis of the correction table stored in the correction table storage.

7. An ultrasound diagnostic device comprising:
the system including the ultrasound probe and the puncture needle according to claim 1; and
a diagnostic apparatus main body connected to the ultrasound probe for the puncture needle, wherein
the diagnostic apparatus main body includes:
  a transmission driving section that supplies a driving signal to the transducer array of the ultrasound probe to transmit ultrasonic beams toward the subject;
  a transmission controller that forms ultrasonic beams by imparting a predetermined transmission delay amount to the driving signal supplied to the transmission driving section;
  a reception signal processor that generates reception data from a reception signal output from the transducer array of the ultrasound probe that received ultrasonic echoes from the subject;
  a phasing addition section that generates a sound ray signal by imparting a predetermined reception delay amount on the reception data and performing addition processing;
  a signal processor that performs attenuation correction in accordance with a focal position of ultrasonic waves on the sound ray signal; and
  a high-speed calculation processor that individually calculates the transmission delay amount, the reception delay amount, and an attenuation correction amount based on the focal position, in accordance with an arrangement of the transducers and the focal position.

8. The ultrasound diagnostic device according to claim 7, wherein the high-speed calculation processor serves as the phasing addition section and the signal processor.

* * * * *